United States Patent [19]
Riedl et al.

[11] Patent Number: 5,922,708
[45] Date of Patent: Jul. 13, 1999

[54] HETEROARYL-OXAZOLIDINONES

[75] Inventors: Bernd Riedl; Dieter Häbich; Andreas Stolle; Martin Ruppelt, all of Wuppertal; Stephan Bartel, Bergisch Gladbach; Walter Guarnieri, Zülpich; Rainer Endermann; Hein-Peter Kroll, both of Wuppertal, all of Germany

[73] Assignee: Bayer Aktiengesellschaft, Leverkusen, Germany

[21] Appl. No.: 08/790,869

[22] Filed: Feb. 3, 1997

[30] Foreign Application Priority Data

Feb. 6, 1996 [DE] Germany ............................ 196 04 224
Nov. 27, 1996 [DE] Germany ............................ 196 49 095

[51] Int. Cl.$^6$ .................... C07D 413/14; C07D 43/04; A61K 31/44; A61K 31/535
[52] U.S. Cl. .................. 514/236.8; 514/342; 514/341; 514/340; 546/153; 546/159; 546/162; 546/171; 546/194; 546/256; 546/268.7; 546/269.1; 546/271.4; 544/333; 544/238; 544/336; 544/356; 544/364; 544/131
[58] Field of Search .......................... 546/153, 159, 546/162, 171, 194, 256, 269.1, 271.4; 514/340, 342, 341, 236.8; 544/131, 333

[56] References Cited

U.S. PATENT DOCUMENTS

| | | | |
|---|---|---|---|
| 4,705,799 | 11/1987 | Gregory ........................... | 514/376 |
| 4,801,600 | 1/1989 | Wang et al. ........................ | 514/376 |
| 4,921,869 | 5/1990 | Wang et al. ........................ | 514/376 |
| 4,942,183 | 7/1990 | Gregory et al. .................... | 514/376 |
| 4,965,268 | 10/1990 | Wang et al. ........................ | 514/253 |
| 5,032,605 | 7/1991 | Wang et al. ........................ | 514/376 |
| 5,130,316 | 7/1992 | Carlson et al. ..................... | 514/255 |
| 5,164,510 | 11/1992 | Brickner et al. .................... | 548/231 |
| 5,182,403 | 1/1993 | Bricner et al. ..................... | 548/231 |
| 5,225,565 | 7/1993 | Brickner et al. .................... | 548/229 |
| 5,254,577 | 10/1993 | Carlson et al. ..................... | 514/376 |
| 5,475,014 | 12/1995 | Akasaka et al. ..................... | 514/367 |
| 5,529,998 | 6/1996 | Häbich et al. ....................... | 514/233.8 |
| 5,561,148 | 10/1996 | Gante et al. ......................... | 514/376 |
| 5,565,571 | 10/1996 | Barbachyn et al. ................... | 546/144 |
| 5,574,055 | 11/1996 | Borgulya et al. ..................... | 514/376 |
| 5,627,181 | 5/1997 | Riedl et al. ......................... | 514/236.8 |

FOREIGN PATENT DOCUMENTS

| | | |
|---|---|---|
| 352781 | 1/1990 | European Pat. Off. . |
| 693491 | 1/1996 | European Pat. Off. . |
| 694543 | 1/1996 | European Pat. Off. . |
| 4425609 | 1/1996 | Germany . |

OTHER PUBLICATIONS

Riedl et al., (CA 124:261021, EP 694543), Jan. 31, 1996.
E.A. ter Laak et al., Antimicrobial Agents and Chemotherapy, vol. 35, No. 2, pp. 228–233 (1991).
J. Swenson et al., Antimicrobial Agents and Chemotherapy, vol. 22, No. 2, pp. 186–192 (1982).
C.H. Park et al., J.Med.Chem. vol. 35, pp. 1156–1165 (1992).

*Primary Examiner*—José G. Dees
*Assistant Examiner*—Sabiha N. Qazi
*Attorney, Agent, or Firm*—Sprung Kramer Schaefer & Briscoe

[57] ABSTRACT

The invention relates to novel heteroaryl-oxazolidinones of the general formula (I):

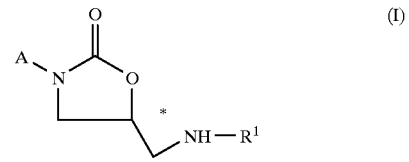

in which the substituents are as defined in the description, to processes for their preparation and to their use as drugs, especially as antibacterial drugs.

11 Claims, No Drawings

HETEROARYL-OXAZOLIDINONES

The present invention relates to novel heteroaryl-oxazolidinones, to processes for their preparation and to their use as drugs, especially as antibacterial drugs.

The publications U.S. Pat. No. 5,254,577, U.S. Pat. No. 4,705,799, EP 311 090, EP 312 000 and C. H. Park et al., J. Med. Chem. 35, 1156 (1992), have disclosed N-aryloxazolidinones with an antibacterial action. 3-(Nitrogen-substituted)-phenyl-5-beta-amidomethyloxazolidin-2-ones are also known from EP 609 905 A1.

Oxazolidinone derivatives with an inhibitory action on monoamine oxidase have been published in EP 609 441 and EP 657 440 and oxazolidinone derivatives acting as adhesion receptor antagonists have been published in EP 645 376.

Oxazolidinone derivatives with an antibacterial action have also been described in our patent applications EP 694 543, EP 693 491, EP 694 544 and EP 697 412.

The present invention relates to novel heteroaryl-oxazolidinones of the general formula (I):

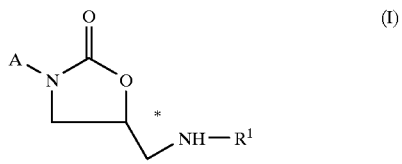

in which $R^1$ is a radical of the formula $D-R^2$, $-CO-R^3$ or $-CO-NR^4R^5$, wherein D is the $CO_2$ or $SO_2$ group, $R^2$ is phenyl or linear or branched alkyl having up to 7 carbon atoms, $R^3$ is trifluoromethyl or linear or branched alkyl having up to 6 carbon atoms which is substituted by halogen or trifluoromethyl, and $R^4$ and $R^5$ are identical or different and are hydrogen, phenyl or linear or branched alkyl having up to 5 carbon atoms, and A is a 6-membered aromatic heterocycle having at least one nitrogen atom and directly bonded via a carbon atom, or a 6-membered bicyclic or tricyclic aromatic radical having at least one nitrogen-containing ring and directly bonded via a carbon atom, or β-carbolin-3-yl or indolizinyl directly bonded via the 6-membered ring, or a 5-membered aromatic heterocycle having up to 3 heteroatoms from the group S, N and/or O and directly bonded via a carbon atom, which heterocycle can additionally have a fused benzene or naphthyl ring, all the rings optionally being substituted in each case by up to 3 identical or different substituents selected from carboxyl, halogen, cyano, mercapto, formyl, trifluoromethyl, nitro, linear or branched alkoxy, alkoxycarbonyl, alkylthio or acyl, each of which has up to 6 carbon atoms, and linear or branched alkyl having up to 6 carbon atoms, which in turn can be substituted by hydroxyl, by linear or branched alkoxy or acyl, each of which has up to 5 carbon atoms, or by a group of the formula $-NR^6R^7$, wherein $R^6$ and $R^7$ are identical or different and are hydrogen, cycloalkyl having 3 to 6 carbon atoms, linear or branched alkyl having up to 5 carbon atoms or phenyl, or, together with the nitrogen atom, form a 5- or 6-membered saturated heterocycle optionally having another heteroatom from the group N, S and/or O, which heterocycle in turn can optionally be substituted, also on another nitrogen atom, by linear or branched alkyl or acyl, each of which has up to 3 carbon atoms, and/or the rings are optionally substituted by a group of the formula $-NR^{6'}R^{7'}$, wherein $R^{6'}$ and $R^{7'}$ are identical or different, are as defined above for $R^6$ and $R^7$ and are identical thereto or different therefrom, and/or the rings are optionally substituted by $(C_2-C_8)$-alkenylphenyl, phenyl or a 5- or 6-membered saturated or unsaturated heterocycle having up to 3 heteroatoms from the group S, N and/or O, which substituents in turn are optionally substituted by a group of the formula $-CO-N^8R^9$, $-NR^{10}R^{11}$, $-NR^{12}-S(O)_2-R^{13}$, $R^{14}R^{15}N-SO_2-$ or $R^{16}-S(O)_a$, wherein a is the number 0, 1 or 2, $R^8$, $R^9$, $R^{12}$, $R^{14}$ and $R^{15}$ are identical or different and are hydrogen, linear or branched alkyl having up to 6 carbon atoms or phenyl, $R^{10}$ and $R^{11}$ are identical or different, are as defined above for $R^6$ and $R^7$ and are identical thereto or different therefrom, and $R^{13}$ and $R^{16}$ are identical or different and are linear or branched alkyl having up to 4 carbon atoms or phenyl which is optionally substituted by linear or branched alkyl having up to 4 carbon atoms, and/or in turn are optionally substituted by up to 2 identical or different substituents selected from carboxyl, halogen, cyano, mercapto, formyl, trifluoromethyl, nitro, phenyl, linear or branched alkoxy, alkoxycarbonyl, alkylthio or acyl, each of which has up to 6 carbon atoms, and linear or branched alkyl having up to 6 carbon atoms, which in turn can be substituted by hydroxyl, by linear or branched alkoxy or acyl, each of which has up to 5 carbon atoms, or by a group of the formula $-NR^{17}R^{18}$, wherein $R^{17}$ and $R^{18}$ are as defined above for $R^6$ and $R^7$ and are identical thereto or different therefrom, and/or the rings are optionally substituted by a radical of the formula

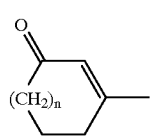

wherein n is the number 0, 1 or 2, and their salts.

The compounds according to the invention can exist in stereoisomeric forms which either behave as image and mirror image (enantiomers) or do not behave as image and mirror image (diastereoisomers). The invention relates both to the enantiomers or diastereoisomers and to their respective mixtures. The racemic forms and the diastereoisomers can be resolved in a known manner into the stereoisomerically pure components.

Biocompatible salts of the novel heteroaryl-oxazolidinones can be salts of the substances according to the invention with mineral acids, carboxylic acids or sulphonic acids. Examples of particularly preferred salts are those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts which may be mentioned are those with conventional bases, for example alkali metal salts (e.g. sodium or potassium salts), alkaline earth metal salts (e.g. calcium or magnesium salts) or ammonium salts derived from ammonia or from organic amines such as, for example, diethylamine, triethylamine, ethyldiisopropylamine, procaine, dibenzylamine, N-methylmorpholine, dihydroabietylamine, 1-ephenamine or methyl-piperidine.

Within the framework of the invention, the heterocycle in the substituent A, in the case of direct bonding to the oxazolidinone skeleton, can on the one hand be a 5-membered aromatic ring which can contain up to 3 oxygen, sulphur and/or nitrogen atoms as heteroatoms and can additionally have a fused benzene or naphthyl ring. Examples which may be mentioned are pyrrolyl, imidazolyl, furyl, thienyl, thiazolyl, oxazolyl, isothiazolyl, isoxazolyl, furazanyl, indolyl, benzo[b]thienyl, naphtho[2,3-b]thienyl, benzo[b]thiazolyl, benzo[b]furanyl or benzo[b]imidazolyl. Pyrrolyl, imidazolyl, furyl, thienyl, isothiazolyl, thiazolyl, isoxazolyl, furazanyl, oxazolyl, benzo[b]thienyl, benzo[b]imidazolyl and benzo[b]thiazolyl are preferred.

Within the framework of the invention, the heterocycle in the substituent A, in the case of direct bonding to the oxazolidinone skeleton, can on the other hand generally also be a 6-membered aromatic heterocycle having at least one nitrogen atom and directly bonded via a carbon atom, or a 6-membered bicyclic or tricyclic aromatic radical having at least one nitrogen-containing ring and directly bonded via a carbon atom, or β-carbolin-3-yl or indolizinyl directly bonded via the 6-membered ring. Examples which may be mentioned are cinnolinyl, pteridinyl, phenanthridinyl, acridinyl, phenanthrolinyl, quinazolinyl, quinoxalinyl, naphthyridinyl, phthalazinyl, quinolyl, isoquinolyl, 4H-quinolizinyl, phenazinyl, pyridyl, pyrazinyl, pyrimidinyl, pyridazinyl, indolizinyl, β-carbolin-3-yl and indolizinyl directly bonded via the 6-membered ring.

In the broader definition of substituents, the heterocycle can also be a 5- or 6-membered saturated or unsaturated ring which can contain up to 3 oxygen, sulphur and/or nitrogen atoms as heteroatoms. Thienyl, furyl, pyrrolyl, pyrazolyl, pyridyl, pyrimidyl, pyrazinyl, pyridazinyl, thiazolyl, oxazolyl, imidazolyl, pyrrolidinyl, piperidinyl or piperazinyl may be mentioned as preferred.

These also include 5- or 6-membered saturated heterocycles bonded via N, which can also contain up to 2 oxygen, sulphur and/or nitrogen atoms as heteroatoms, examples being piperidyl, morpholinyl, piperazinyl or pyrrolidinyl. Piperidyl and pyrrolidinyl are particularly preferred.

Within the framework of the definition indicated above, hydroxyl-protecting group is generally a protecting group selected from the following: trimethylsilyl, triisopropylsilyl, tert-butyl-dimethylsilyl, benzyl, benzyloxycarbonyl, 2-nitrobenzyl, 4-nitrobenzyl, tert-butoxycarbonyl, allyloxycarbonyl, 4-methoxybenzyl, 4-methoxybenzyloxycarbonyl, tetrahydropyranyl, formyl, acetyl, trichloroacetyl, 2,2,2-trichloroethoxycarbonyl, methoxyethoxymethyl, [2-(trimethylsilyl)ethoxy]methyl, benzoyl, 4-methylbenzoyl, 4-nitrobenzoyl, 4-fluorobenzoyl, 4-chlorobenzoyl or 4-methoxybenzoyl. Acetyl, tert-butyldimethylsilyl or tetrahydropyranyl is preferred.

Within the framework of the invention, amino-protecting groups are the conventional amino-protecting groups used in peptide chemistry.

These preferably include benzyloxycarbonyl, 2,4-dimethoxybenzyloxycarbonyl, 4-methoxybenzyloxycarbonyl, methoxycarbonyl, ethoxycarbonyl, tert-butoxycarbonyl, allyloxycarbonyl, phthaloyl, 2,2,2-trichloroethoxycarbonyl, 9-fluorenylmethoxycarbonyl, formyl, acetyl, 2-chloroacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl, 4-methoxyphenyl or triphenylmethyl.

Preferred compounds of the general formula (I) are those in which $R^1$ is a radical of the formula $D-R^2$, $-CO-R^3$ or $-CO-NR^4R^5$, wherein D is the $CO_2$ or $SO_2$ group, $R^2$ is phenyl or linear or branched alkyl having up to 5 carbon atoms, $R^3$ is trifluoromethyl or linear or branched alkyl having up to 5 carbon atoms which is substituted by fluorine, chlorine, bromine or trifluoromethyl, and $R^4$ and $R^5$ are identical or different and are hydrogen, phenyl or linear or branched alkyl having up to 4 carbon atoms, and A is cinnolinyl, pteridinyl, acridinyl, quinazolinyl, quinoxalinyl, naphthyridinyl, phthalazinyl, quinolyl, isoquinolyl, pyridyl, pyrazinyl, pyrimidinyl or pyridazinyl bonded via a carbon atom, or pyrrolyl, imidazolyl, furyl, thienyl, thiazolyl, oxazolyl, isothiazolyl, isoxazolyl or furazanyl directly bonded via a carbon atom, or indolyl, benzo[b]thienyl, naphtho[2,3-b]thienyl, benzo[b]thiazolyl, benzo[b]-imidazolyl or benzo[b]furanyl also directly bonded via a carbon atom of the 5-membered ring, which substituents are optionally substituted by up to 3 identical or different substituents selected from fluorine, chlorine, bromine, linear or branched alkyl, acyl or alkoxy, each of which has up to 5 carbon atoms, phenyl, pyrimidyl, pyridazinyl and pyridyl, which in turn can be substituted by linear or branched alkyl, alkoxy or acyl, each of which has up to 5 carbon atoms, or by a group of the formula $-NR^6R^7$, wherein $R^6$ and $R^7$ are identical or different and are hydrogen, phenyl, cyclopropyl, cyclobutyl, cyclopentyl, cyclohexyl or linear or branched alkyl having up to 4 carbon atoms, and their salts.

Particularly preferred compounds according to the invention of the general formula (I) are those in which $R^1$ is a radical of the formula $D-R^2$, $-CO-R^3$ or $-CO-NR^4R^5$, wherein D is the $CO_2$ or $SO_2$ group, $R^2$ is phenyl or linear or branched alkyl having up to 4 carbon atoms, $R^3$ is trifluoromethyl or linear or branched alkyl having up to 3 carbon atoms which is substituted by fluorine, chlorine, bromine or trifluoromethyl, and $R^4$ and $R^5$ are identical or different and are hydrogen, phenyl or linear or branched alkyl having up to 3 carbon atoms, and A is thienyl, pyridyl or quinolyl, each of which is optionally substituted by up to 2 identical or different substituents selected from chlorine, bromine, linear or branched alkyl or alkoxy, each of which has up to 5 carbon atoms, phenyl, pyridazinyl, pyrimidyl and pyridyl, which in turn can be substituted by linear or branched alkyl, alkoxy or acyl, each of which has up to 5 carbon atoms, or by a group of the formula —$NR^6R^7$, wherein $R^6$ and $R^7$ are identical or different and are hydrogen, phenyl, cyclopropyl, cyclobutyl, cyclopentyl, cyclohexyl or linear or branched alkyl having up to 3 carbon atoms, and their salts.

Other particularly preferred compounds according to the invention of the general formula (I) are those in which $R^1$ is a radical of the formula D—$R^2$, wherein D is the $SO_2$ group and $R^2$ is defined as indicated above.

Other particularly preferred compounds according to the invention of the general formula (I) are those in which $R^1$ is a radical of the formula D—$R^2$, wherein D is the $CO_2$ group and $R^2$ is defined as indicated above.

Other particularly preferred compounds according to the invention of the general formula (I) are those in which $R^1$ is a radical of the formula CO—$R^3$, wherein $R^3$ is defined as indicated above.

Other particularly preferred compounds according to the invention of the general formula (I) are those in which $R^1$ is a radical of the formula CO—$NR^4R^5$, wherein $R^4$ and $R^5$ are defined as indicated above.

Other particularly preferred compounds of the general formula (I) are those in which A is thienyl which can optionally be substituted as indicated above.

Other particularly preferred compounds of the general formula (I) are those in which A is quinolyl which can optionally be substituted as indicated above.

Other particularly preferred compounds of the general formula (I) are those in which A is pyridyl which can optionally be substituted as indicated above.

Examples of these compounds which are very particularly preferred are those in which the pyridyl is substituted by pyrimidyl or pyridyl, each of which in turn can be substituted by linear or branched alkyl or alkoxy, each of which has up to 5 carbon atoms.

A process for the preparation of the compounds according to the invention of the general formula (I) has also been found which is characterized in that compounds of the general formula (II):

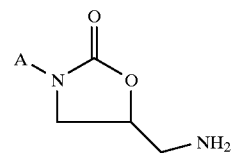

(II)

in which

A is as defined above, are reacted with compounds of the general formula (III):

$R^1$-E  (III)

in which $R^1$ is as defined above and

E is halogen or linear or branched alkylthio, alkoxy or hydroxyalkoxycarbonyl, each of which has up to 5 carbon atoms, in inert solvents, optionally in the presence of a base.

The process according to the invention can be exemplified by the following equation:

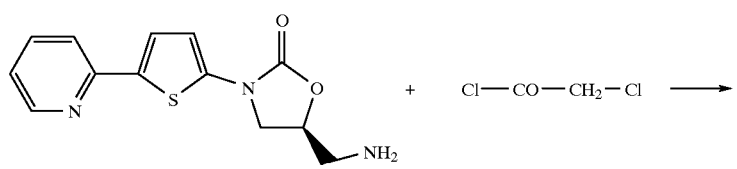

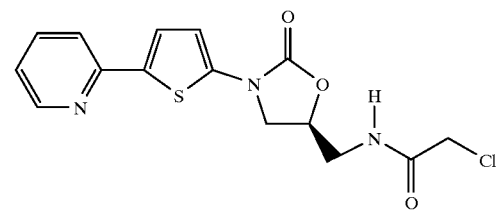

Suitable solvents, depending on the individual process steps, are the conventional solvents which are not affected by the reaction conditions. These preferably include alcohols such as methanol, ethanol, propanol or isopropanol, ethers such as diethyl ether, dioxane, 1,2-dimethoxyethane, tetrahydrofuran, glycol dimethyl ether or tert-butyl methyl ether, ketones such as acetone or butanone, amides such as dimethylformamide or hexamethylphosphorotriamide, hydrocarbons such as hexane, benzene, dichlorobenzene, xylene or toluene, dimethyl sulphoxide, acetonitrile, ethyl acetate, halogenated hydrocarbons such as methylene chloride, chloroform or carbon tetrachloride, pyridine, picoline or N-methylpiperidine. Mixtures of said solvents can also be used.

Suitable bases, depending on the individual process steps, are the conventional inorganic or organic bases. These preferably include alkali metal hydroxides such as, for example, sodium or potassium hydroxide, alkali metal carbonates such as sodium or potassium carbonate, alkali metal alcoholates such as, for example, sodium or potassium methylate or sodium or potassium ethylate, organic amines such as ethyldiisopropylamine, triethylamine, picoline, pyridines or N-methylpiperidine, amides such as sodium amide or lithium diisopropylamide, lithium N-silylalkylamides such as, for example, lithium N-(bis) triphenylsilylamide, or lithium alkyls such as n-butyllithium.

The base is used in an amount of 1 mol to 10 mol, preferably of 1 mol to 3 mol, based on 1 mol of the compounds of the general formula (III).

The reaction is generally carried out at normal, elevated or reduced pressure (e.g. 0.5 to 5 bar). It is generally carried out at normal pressure.

The compounds of the general formula (III) are known or can be prepared by conventional methods.

Some of the compounds of the general formula (II) are novel and they can be prepared by converting compounds of the general formula (IV):

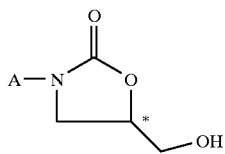

(IV)

in which

A is as defined above, by reaction with $(C_1-C_4)$-alkyl- or phenyl-sulphonyl chlorides, in inert solvents and in the presence of a base, to the corresponding compounds of the general formula (V):

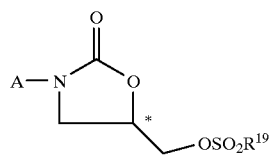

(V)

in which

A is as defined above and $R^{19}$ is $C_1-C_4$-alkyl, then preparing the azides of the general formula (VI):

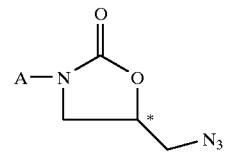

(VI)

in which

A is as defined above, with sodium azide in inert solvents, and, in a subsequent step, converting said azides to the amines by reaction with $(C_1-C_4\text{-alkyl-O})_3$—P or $PPh_3$, preferably $(CH_3O)_3P$, in inert solvents and with acids.

Suitable solvents, depending on the individual process steps, are the conventional solvents which are not affected by the reaction conditions. These preferably include alcohols such as methanol, ethanol, propanol or isopropanol, ethers such as diethyl ether, dioxane, 1,2-dimethoxyethane, tetrahydrofuran, glycol dimethyl ether or tert-butyl methyl ether, ketones such as acetone or butanone, amides such as dimethylformamide or hexamethylphosphorotriamide, hydrocarbons such as hexane, benzene, dichlorobenzene, xylene or toluene, dimethyl sulphoxide, acetonitrile, ethyl acetate, halogenated hydrocarbons such as methylene chloride, chloroform or carbon tetrachloride, pyridine, picoline or N-methylpiperidine. Mixtures of said solvents can also be used.

Suitable bases, depending on the individual process steps, are the conventional inorganic or organic bases. These preferably include alkali metal hydroxides such as, for example, sodium or potassium hydroxide, alkali metal carbonates such as sodium or potassium carbonate, alkali metal alcoholates such as, for example, sodium or potassium methylate or sodium or potassium ethylate, organic amines such as ethyldiisopropylamine, triethylamine, picoline, pyridines or N-methylpiperidine, amides such as sodium amide or lithium diisopropylamide, lithium N-silylalkylamides such as, for example, lithium N-(bis) triphenylsilylamide, or lithium alkyls such as n-butyllithium.

The base is used in an amount of 1 mol to 10 mol, preferably of 1 mol to 3 mol, based on 1 mol of the compounds of the general formula (IV).

All the reactions are generally carried out at normal, elevated or reduced pressure (e.g. 0.5 to 5 bar). They are generally carried out at normal pressure.

The azides are reduced with $(CH_3O)_3P$ and hydrochloric acid.

The reduction is generally carried out in a temperature range from −50° C. to the boiling point of the solvent in question, preferably from −20° C. to +90° C.

Suitable solvents here are any inert organic solvents which are not affected by the reaction conditions. These preferably include alcohols such as methanol, ethanol, propanol or isopropanol, ethers such as diethyl ether, dioxane, tetrahydrofuran, glycol dimethyl ether or diethylene glycol dimethyl ether, amides such as hexamethylphosphorotriamide or dimethylformamide, or acetic acid. It is also possible to use mixtures of said solvents.

The compounds of the general formulae (V) and (VI) are novel and can be prepared as described above.

Some of the compounds of the general formula (IV) are novel and they can be prepared by

[B] reacting compounds of the general formula (VII) or (VIII):

A—N=C=O (VII) or A—CO—N₃ (VIII)

in which

A is as defined above, with lithium bromide/(C₄H₉)₃P(O) and epoxides of the general formula (IX):

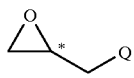
(IX)

in which

Q is $C_{1-C_6}$-acyloxy, in inert solvents, optionally in the presence of a base, and freeing the hydroxyl group by a typical ester saponification or by a typical transesterification, or

[C] reacting compounds of the general formula (X):

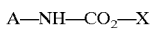
A—NH—CO₂—X (X)

in which

A is as defined above and

X is a typical protecting group, preferably benzyl, in inert solvents and in the presence of a base, for example lithium alkyls, lithium N-alkylamides or lithium N-silylalkylamides, preferably n-butyllithium, with epoxides of the general formula (IX), or first converting compounds of the general formula (VIII), by cleavage of the nitrogen in alcohols, to the compounds of the general formula (Xa):

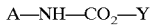
A—NH—CO₂—Y (Xa)

in which

A is as defined above and

Y is linear or branched $C_2$–$C_6$-alkyl, preferably n-butyl, and, in a second step, reacting said compounds of the general formula (Xa), as described under [B], in inert solvents and in the presence of a base, preferably lithium N-alkylamides or N-silylalkylamides or n-butyllithium, with epoxides of the general formula (IX), or

[D] either directly reacting compounds of the general formula (XI):

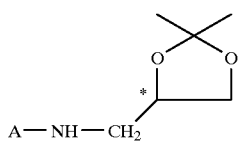
(XI)

in which

A is as defined above, with acids and diethyl carbonate, or first preparing the compounds of the general formula (XII):

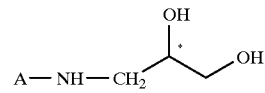
(XII)

in which

A is as defined above, by reacting the compounds of the general formula (XI) with acids, and then cyclizing said compounds of the general formula (XII), in the presence of an auxiliary, in inert solvents.

Suitable solvents, depending on the individual process steps, are the conventional solvents which are not affected by the reaction conditions. These preferably include alcohols such as methanol, ethanol, propanol or isopropanol, ethers such as diethyl ether, dioxane, 1,2-dimethoxyethane, tetrahydrofuran, glycol dimethyl ether or tert-butyl methyl ether, ketones such as acetone or butanone, amides such as dimethylformamide or hexamethylphosphorotriamide, hydrocarbons such as hexane, benzene, dichlorobenzene, xylene or toluene, dimethyl sulphoxide, acetonitrile, ethyl acetate, halogenated hydrocarbons such as methylene chloride, chloroform or carbon tetrachloride, pyridine, picoline or N-methylpiperidine. Mixtures of said solvents can also be used.

Suitable bases, depending on the individual process steps, are the conventional inorganic or organic bases. These preferably include alkali metal hydroxides such as, for example, sodium or potassium hydroxide, alkali metal carbonates such as sodium or potassium carbonate, alkali metal alcoholates such as, for example, sodium or potassium methylate or sodium or potassium ethylate, organic amines such as ethyldiisopropylamine, triethylamine, picoline, pyridines or N-methylpiperidine, amides such as sodium amide or lithium diisopropylamide, lithium N-silylalkylamides such as, for example, lithium N-(bis) triphenylsilylamide, or lithium alkyls such as n-butyllithium.

The base is used in an amount of 1 mol to 10 mol, preferably of 1 mol to 3 mol, based on 1 mol of the compounds of the general formulae (IX) and (X).

All the reactions are generally carried out at normal, elevated or reduced pressure (e.g. 0.5 to 5 bar). They are generally carried out at normal pressure.

Process [B] is preferably carried out in xylene or dichlorobenzene, optionally in the presence of triethylamine, under reflux.

The base-catalysed transesterification is carried out with one of the alcohols listed above, preferably methanol, in a temperature range from –10° C. to +40° C., preferably at room temperature.

Suitable bases are generally sodium hydrogen carbonate, sodium methylate, hydrazine hydrate, potassium carbonate or caesium carbonate. Caesium carbonate is preferred.

Process [C] is carried out in one of the ethers listed above with lithium alkyl compounds or lithium N-silylamides, for example n-butyllithium, lithium diisopropylamide or lithium bis-trimethylsilylamide, preferably in tetrahydrofuran with lithium bis-trimethylsilylamide or n-butyllithium, in a temperature range from –100° C. to +20° C., preferably from –75° C. to –40° C.

The alcohols listed above are preferentially suitable for the 1st step of process [D] and tetrahydrofuran is preferentially suitable for the subsequent cyclization.

Suitable bases for the cyclization are preferably the lithium N-silylalkylamide compounds listed above or n-butyllithium. n-Butyllithium is particularly preferred.

The first reaction step is carried out at the boiling point of the alcohol in question and the cyclization is carried out in a temperature range from −70° C. to room temperature.

The cyclization [D] is carried out in the presence of an auxiliary and/or in the presence of an acid.

Suitable acids are generally inorganic acids such as, for example, hydrochloric acid or sulphuric acid, organic carboxylic acids having 1–6 C atoms which are optionally substituted by fluorine, chlorine and/or bromine, examples being acetic acid, trifluoroacetic acid, trichloroacetic acid or propionic acid, or sulphonic acids having $C_1$–$C_4$-alkyl radicals or aryl radicals, examples being methanesulphonic acid, ethanesulphonic acid, benzenesulphonic acid or toluenesulphonic acid. Hydrochloric acid is particularly preferred.

The acid is used in an amount of 1 mol to 10 mol, preferably of 1 mol to 2 mol, based on 1 mol of the compounds of the general formula (XI).

Suitable auxiliaries are the conventional reagents such as phosgene, carbonyldiimidazole, diethyl carbonate or trichloromethyl chloroformate. Carbonyldiimidazole, diethyl carbonate or trichloromethyl chloroformate is preferred.

Suitable solvents are the halogenated hydrocarbons listed above. Methylene chloride is preferred.

The compounds of the general formula (VIII) are known or can be prepared by conventional methods.

Most of the compounds of the general formula (XII) are novel and they can be prepared for example as described above.

Some of the compounds of the general formula (VII) are known or they are novel and can then be prepared for example by reacting the appropriate amines with trichloroethyl chloroformate in one of the solvents listed above, preferably xylene, at the reflux temperature.

Some of the compounds of the general formula (VIII) are known or they are novel and can then be prepared for example by reacting the appropriate carboxylic acids with isobutyl chloroformate/acetone, with sodium azide/water, with diphenylphosphoryl azide/tetrahydrofuran or with xylene or methylene chloride, in the presence of one of the bases indicated above, preferably triethylamine, at −10° C. to room temperature.

Some of the compounds of the general formulae (X) and (Xa) are known or they are novel and can be prepared either by cleaving the nitrogen from the appropriate carboxylic acid azides and reacting the product with the appropriate alcohols, or by reacting the appropriate amines with chloroformic acid esters, preferably benzyl chloroformate, in one of the solvents listed above, preferably tetrahydrofuran or dioxane, in a temperature range from −10° C. to 200° C., preferably from 0° C. to 150° C.

The minimum inhibitory concentrations (MIC) were determined by the serial dilution method on Iso-Sensitest agar (Oxoid). For each test substance a series of agar plates were prepared which contained decreasing concentrations of the active substance, obtained by twofold dilution from one plate to the next. The agar plates were inoculated with a Multipoint inoculator (Denley). Inoculation was effected using overnight cultures of the pathogens which had been diluted beforehand so that each inoculation point contained ca. $10^4$ colony forming particles. The inoculated agar plates were incubated at 37° C. and the bacterial growth was evaluated after ca. 20 hours. The MIC value (μg/ml) indicates the lowest active substance concentration at which no growth was detectable with the naked eye.

| | | | MIC values (μg/ml) | | | | |
|---|---|---|---|---|---|---|---|
| Ex. no. | Staph. 133 | Staph. 48N | Staph. 25701 | Staph. 9TV | E. coli Neumann | Klebs. 57 USA | Psdm. Bonn |
| 10 | 4 | 4 | 4 | 2 | >64 | >64 | >64 |
| 13 | 2 | 2 | 2 | 2 | >64 | >64 | >64 |
| 14 | 2 | 2 | 2 | 1 | >64 | >64 | >64 |
| 17 | 4 | 4 | 2 | 4 | >64 | >64 | >64 |
| 18 | 2 | 4 | 4 | 1 | >64 | >64 | >64 |
| 20 | 2 | 2 | 2 | 2 | >64 | >64 | >64 |
| 25 | 2 | 2 | 2 | 1 | >64 | >64 | / |

For rapidly growing mycobacteria the MIC were determined on the basis of the broth microdilution method described by Swenson [cf. J. M. Swenson, C. Thomberry, U. A. Silcox, Rapidly growing mycobacteria. Testing of susceptibility to 34 antimicrobial agents by broth microdilution. Antimicrobial Agents and Chemotherapy, vol. 22, 186–192 (1982)]. The brain-heart extract medium treated with 0.1 vol.% of Tween 80 was an exception.

The mycobacterial strains used were obtained from the DSM (Deutsche Sammlung von Mikroorganismen (German Collection of Microorganisms), Brunswick). They were incubated in a moist chamber at 37° C.

The MIC values were evaluated after 2–4 days, when the preparation-free controls were opaque due to growth. The MIC value is defined as the lowest concentration of preparation which completely inhibits macroscopically visible growth.

| | MIC values: Mycobacterium smegmatis | |
|---|---|---|
| Bacterium | DSM 43061 | DSM 43078 |
| Inoculum [/ml] | 2.20E + 04 | 4.20E + 04 |
| Ex. no. | | |
| 14 | 4 | 4 |
| 17 | 4 | 4 |
| Isoniazid | 4 | 2 |
| Streptomycin | 4 | 4 |

MIC determination with Mycoplasma pneumoniae

Mycoplasma pneumoniae strain PI 1428 was cultured under aerobic conditions in PPLO medium to which 1% of glucose, 2.5% of yeast extract, 20% of donor horse serum and 0.002% of phenol red had been added. The MIC were determined on the basis of the method of serial microdilution in a liquid medium, described by ter Laak et al. (E. A. ter Laak, A. Pijpers, J. H. Noordergraaf, E. Schoevers, J. H. M. Verheijden: Comparison of Methods for in vitro Testing of Susceptibility of Porcine Mycoplasma Species to Antimicrobial Agents; Antimicrobial Agents and Chemotherapy, vol. 35, 228–233 (1991)). At the point when the medium of the preparation-free control started to change colour from red to yellow, 10 vol.% of alamar blue was added. Incubation at 37° C. was continued for ca. 10 hours and the MIC was defined as the value at which the blue colour of the medium with the smallest concentration of preparation remained unchanged.

| Ex. no. | MIC (mg/ml) |
|---|---|
| 13 | 8 |
| 14 | 8 |

The compounds according to the invention of general formula (I) have a low toxicity and a broad antibacterial spectrum, especially against Gram-positive bacteria and mycobacteria, Haemophilus influenzae and anaerobic bacteria for rapidly growing mycobacteria. These properties enable them to be used as chemotherapeutic active substances in human and veterinary medicine.

The compounds according to the invention are particularly effective against bacteria and bacterioid microorganisms such as mycoplasmata. They are therefore particularly suitable in human and veterinary medicine for the prophylaxis and chemotherapy of local and systemic infections caused by such pathogens.

The present invention includes pharmaceutical formulations which contain one or more compounds according to the invention in addition to non-toxic, inert, pharmaceutically acceptable excipients, or which consist of one or more active substances according to the invention, as well as processes for the preparation of these formulations.

The active substance or substances an optionally also be present in microencapsulated form in one or more of the excipients indicated above.

The therapeutically active compounds should preferably be present in the abovementioned pharmaceutical formulations in a concentration of about 0.1 to 99.5% by weight, preferably of about 0.5 to 95% by weight, of the total mixture.

In addition to the compounds according to the invention, the abovementioned pharmaceutical formulations can also contain other pharmaceutical active substances.

In general it has proved advantageous, in both human and veterinary medicine, to administer the active substance or substances according to the invention in total amounts of about 0.5 to about 500 mg/kg of body weight, preferably 5 to 100 mg/kg of body weight, every 24 hours, optionally in the form of several single doses, in order to achieve the desired results. A single dose preferably contains the active substance or substances according to the invention in amounts of about 1 to about 80 mg/kg of body weight, especially 3 to 30 mg/kg of body weight.

To broaden the spectrum of action and increase the action, the compounds according to the invention can also be combined with other antibiotics.

Annex to the experimental section

List of solvent mixtures used for chromatography

I dichloromethane:methanol
II toluene:ethyl acetate
III acetonitrile:water
IV ethyl acetate
V petroleum ether:ethyl acetate
VI $CH_2Cl_2$:MeOH:$NH_{3(aq)}$
VII $CH_2Cl_2$:MeOH Abbreviations Z benzyloxycarbonyl
Boc tert-butoxycarbonyl
DMF dimethylformamide
Ph phenyl
Me methyl
THF tetrahydrofuran
CDI carbonyldiimidazole
DCE dichloroethane
Starting compounds

EXAMPLE I

5-Bromo-2-isocyanato-pyridine hydrochloride

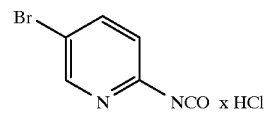

78.0 ml (0.64 mol) of trichloroethyl chloroformate are added dropwise at the boil to a stirred solution of 100 g (0.58 mol) of 2-amino-5-bromopyridine in 400 ml of 1,2-dichloroethane. When the addition has ended, the mixture is refluxed for 2 h and then allowed to cool to room temperature. The precipitate formed is filtered off, washed thoroughly with 100 ml of 1,2- dichloroethane and dried under high vacuum over sodium hydroxide to give 98.3 g (72%) of the title compound in the form of a yellow solid.

M.p.: 248–254° C. (decomp.)

$R_f$=0.23 (ethyl acetate)

MS (EI) m/z=198 (M)$^+$

EXAMPLE II (5R)-3-(5-Bromo-pyridin-2-yl)-5-butyryloxy-methyl-oxazolidin-2-one

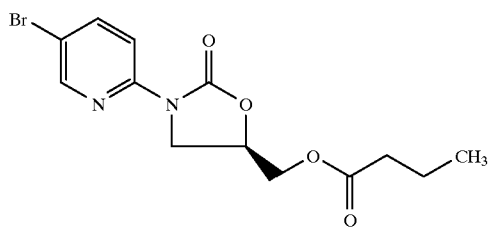

A suspension of 2.17 g (25 mmol) of lithium bromide and 5.46 g (25 mmol) of tributylphosphine oxide in 73 ml of xylene is boiled for 1 h in a water separator. A mixture of 58.5 ml (0.42 mol) of triethylamine and 66.6 g (0.42 mol) of (R)-glycidyl butyrate is added dropwise at the boil. 98.2 g (0.42 mol) of the compound of Example I are simultaneously added in portions over 20 min. When the addition has ended, the mixture is stirred for a further 1 h under reflux. It is allowed to cool to room temperature and the solvent is evaporated off under vacuum. The residue is chromatographed on 1 kg of silica gel (toluene:ethyl acetate 95:5) to give 37.9 g (26%) of the title compound in the form of an oil.

$R_f$=0.43 (toluene:ethyl acetate 4:1)

MS (FAB) m/z=343 (M+H)$^+$ $^1$H NMR (250 MHz, DMSO-d$_6$): δ=0.81 (t, J=7 Hz, 3H, C$\underline{H}_3$CH$_2$); 1.5 (m, 2H, CH$_3$C$\underline{H}_2$CH$_2$CO); 2.29 (t, J=7 Hz, 2H, CH$_3$CH$_2$C$\underline{H}_2$CO); 3.91 (dd, J=7 Hz, 10 Hz, 1H, H-4 trans); 4.25 (dd, J=9 Hz, 10 Hz, 1H, H-4 cis); 4.36 (m, 2H, CH$_2$O); 4.97 (m, 1H, H-5); 8.08 (d, J=1 Hz, 2H, pyridyl H-3,4); 8.50 (d, J=1 Hz, pyridyl H-6).

EXAMPLE III (5R)-3-(5-Bromo-pyridin-2-yl)-5-hydroxymethyl-oxazolidin-2-one

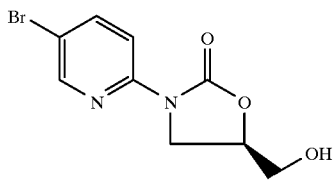

185 mg (0.57 mmol) of caesium carbonate are added to a solution of 19.6 g (57.3 mmol) of the compound of Example I in 125 ml of anhydrous methanol and the mixture is stirred for 5 h at room temperature. The solvent is evaporated off under vacuum and the residue is stirred with 30 ml of ether. The precipitate is filtered off, washed with 25 ml of water and 5 ml of ether and dried under high vacuum to give 10.73 g (69%) of the title compound in the form of light-coloured crystals.

M.p.: 0.09 (toluene:ethyl acetate 4:1)
MS (DCI, $NH_3$) m/z=273 $(M+H)^+$
$^1$H NMR (200 MHz, $CD_3OD$): $\delta$=3.68 (d, J=5.9 Hz, 1H, $CH_2O$); 3.87 (dd, J=4, 9 Hz, 1H, $CH_2O$); 4.06 (dd, J=7, 10 Hz, 1H, H-4 trans); 4.26 (dd, J=9, 10 Hz, 1H, H-4 cis); 4.75 (m, 1H, H-5); 7.92 (dd, J=1.5 Hz, 10 Hz, 1H, pyridyl H-3); 8.12 (d, J=10 Hz, 1H, pyridyl H-4); 8.40 (d, J=1.5 Hz, 1H, pyridyl H-6).

EXAMPLE IV 5-(2-Pyridyl)-thiophene-2-carboxylic acid azide

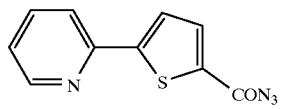

20 g (97.45 mmol) of 5-(2-pyridyl)-thiophene-2-carboxylic acid are dissolved in 200 ml of acetone, 15.94 ml (115 mmol) of triethylamine are added and the reaction solution is cooled to 0° C. A solution of 14.85 ml (115 mmol) of isobutyl chloroformate in 88 ml of acetone is slowly added dropwise, with stirring. After 1 h at 0° C., a solution of 9.5 g (146 mmol) of sodium azide in 44 ml of water is added dropwise and the reaction mixture is subsequently stirred for 1 h at 0° C. and allowed to warm up to room temperature. It is poured all at once into ice-water and the product is filtered off with suction and reacted further as such.

Yield: 21 g of moisture-containing powder

EXAMPLE V 5-(2-Pyridyl)-butoxycarbonylamino-thiophene

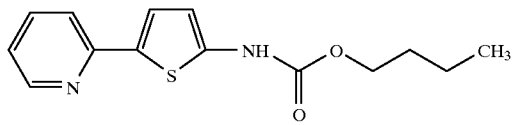

21 g of the compound of Example IV are introduced in portions into 400 ml of boiling n-butanol. When the evolution of gas has ceased, the mixture is stirred for 15 min under reflux. After cooling to room temperature, it is concentrated and the residue is stirred with ether, filtered off with suction and dried at 50° C. in a circulating-air drying cabinet.

Yield: 18.8 g (75% of theory)

$^1$H NMR (200 MHz, DMSO-$d_6$): $\delta$=10.8 (s, 1H); 8.45 (d, J=5 Hz, 1H); 7.68–7.85 (m, 2H); 7.5 (d, J=5 Hz, 1H); 7.1–7.2 (m, 1H); 6.57 (d, J=5 Hz, 1H); 4.14 (t, J=7 Hz, 2H); 1.62 (q, J=7 Hz, 2H); 1.39 (h, J=7 Hz, 2H); 0.92 (t, J=7 Hz, 3H).

EXAMPLE VI (5R)-3-(5-(2-Pyridyl)-thien-2-yl)-5-hydroxymethyl-oxazolidin-2-one

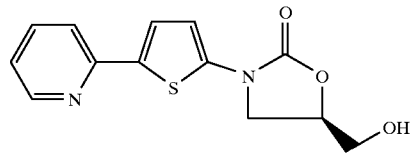

18.8 g (68 mmol) of the compound of Example V are dissolved in 190 ml of absolute THF, 10 mg of 1,10-phenanthroline hydrate are added and the mixture is cooled to −70° C. Ca. 27 ml of a 2.5N solution of n-butyllithium in hexane are then slowly added dropwise until the colour changes to red. 9.6 ml (68 mmol) of (R)-glycidyl butyrate are then added dropwise. The mixture is allowed to warm up to room temperature, saturated ammonium chloride solution is added, the organic phase is separated off and the aqueous phase is extracted twice with methylene chloride. The combined organic phases are dried ($Na_2SO_4$) and concentrated. The residue is stirred with ether and filtered off with suction.

Yield: 15.3 g (81.5% of theory)

$R_f$=0.06 ($CH_2Cl_2$:$CH_3OH$=100:3)

M.p.: 191° C.

$^1$H NMR (200 MHz, DMSO-$d_6$): $\delta$=8.45 (d, J=5 Hz, 1H); 7.7–7.9 (m, 2H); 7.6 (d, J=5 Hz, 1H); 7.15–7.25 (m, 1H); 6.58 (d, J=5 Hz, 1H); 5.28 (t, J=7 Hz, 1H); 4.77–4.9 (m, 1H); 4.13 (dd, J=10 Hz, 9 Hz, 1H); 3.86 (dd, J=10 Hz, 6 Hz, 1H); 3.55–3.78 (m, 2H).

The compounds listed in Table I are prepared analogously to the instructions of Examples I to VI:

TABLE I

[Structure: A-N attached to oxazolidin-2-one with CH2OH substituent at 5-position]

| Ex. no. | A | M.p. (° C.) | R$_f$/Solvent (ratio) | Yield (% of theory) |
|---|---|---|---|---|
| VII | [4-(5-methylthiophen-2-yl)pyridine] | 209 with decomp. | — | 61 |
| VIII | [3-(5-methylthiophen-2-yl)pyridine] | 185 | — | 71 |
| IX | [2,6-dimethylpyridine, attached at 3-position] | 144 | 0.32, I (95:5) | 78 |
| X | [3-methylthiophene] | 132 | — | 79 |
| XI | [6-methylquinoline] | 165 | 0.1, V (1:4) | 45 |

EXAMPLE XII (5R)-3-(5-Bromo-pyridin-2-yl)-5-methanesulphonyloxy-methyl-oxazolidin-2-one

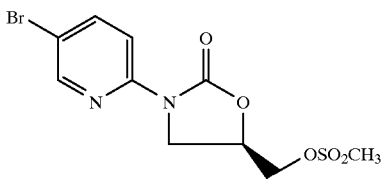

3.27 ml (42.28 mmol) of methanesulphonyl chloride are added slowly to a stirred solution, cooled to 0° C., of 10.5 g (38.44 mmol) of the compound of Example III and 6.40 ml (46.14 mmol) of triethylamine in 36 ml of anhydrous dichloromethane. The mixture is subsequently stirred for 10 min at 0–5° C. and then stirred into 50 ml of ice-water. The organic phase is separated off, washed with 20 ml of saturated NaHCO$_3$ solution and 20 ml of ice-water and dried over MgSO$_4$. The solvent is evaporated off under vacuum and the residue is stirred with 50 ml of ether, filtered off with suction and dried under high vacuum to give 12.8 g (95%) of the title compound in the form of colourless crystals.

M.p.: 138–138.5° C.

R$_f$=0.65 (dichloromethane:methanol 95:5)

MS (DCI, NH$_3$) m/z=351 (M+H)$^+$ $^1$H NMR (250 MHz, DMSO-d$_6$): δ=3.25 (s, 3H, OSO$_2$CH$_3$); 3.91 (dd, J=7, 10 Hz, 1H, H-4 trans); 4.27 (dd, J=10, 10 Hz, 1H, H-4 cis); 4.52 (m, 2H, CH$_2$O); 5.02 (m, 1H, H-5); 8.09 (s, 2H, pyridyl H-3,4); 8.52 (s, 1H, pyridyl H-6).

EXAMPLE XIII (5R)-3-(5-Bromo-pyridin-2-yl)-5-azidomethyl-oxazolidin-2-one

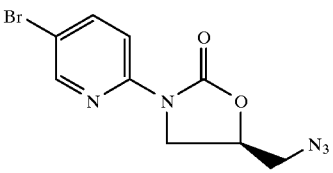

3.01 g (46.28 mmol) of sodium azide are added to a stirred solution of 12.5 g (35.6 mmol) of the compound of Example XII in 48 ml of anhydrous DMF and the mixture is stirred for 3 h at 70° C. It is allowed to cool to room temperature and stirred into 100 ml of ice-water. The precipitate formed is filtered off, washed with 50 ml of water and 20 ml of petroleum ether and dried in air to give 10.1 g (95%) of the title compound in the form of light-coloured crystals.

M.p.: 64–67° C.

R$_f$=0.63 (toluene:ethyl acetate 2:3)

MS (DCI, NH$_3$) m/z=298 (M+H)$^+$ $^1$H NMR (250 MHz, DMSO-d$_6$): δ=3.73 (m, 2H, CH$_2$N$_3$); 3.87 (dd, J=6, 8 Hz, 1H, H-4 trans); 4.22 (dd, J=8, 8 Hz, 1H, H-4 cis); 4.92 (m, 1H, H-5); 8.08 (s, 2H, pyridyl H-3,4); 8.51 (s, 1H, pyridyl H-6).

EXAMPLE XIV (5S)-3-(5-Bromo-pyridin-2-yl)-5-aminomethyl-oxazolidin-2-one hydrochloride

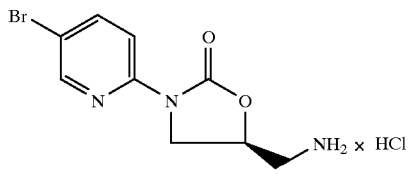

A stirred solution of 10.1 g (33.9 mmol) of the compound of Example XIII in 16.5 ml of 1,2-dimethoxyethane is heated to 50° C. 4.68 ml (4.70 mmol) of trimethyl phosphite are slowly added dropwise (evolution of gas) and, when the addition has ended, the mixture is stirred for a further 2 h at 90° C. 6.6 ml of 6N HCl are then added dropwise and the mixture is stirred for a further 2 h at 90° C. It is allowed to cool to room temperature and the precipitate is filtered off, washed with 2×10 ml of 1,2-dimethoxyethane and dried under high vacuum over NaOH to give 8.9 g (85%) of the title compound in the form of colourless crystals.

M.p.: 260–262° C.

R$_f$=0.53 (acetonitrile:water 4:1)

MS (EI) m/z=271 (M$^+$)

$^1$H NMR (250 MHz, DMSO-d$_6$): δ=3.28 (m, 2H, CH$_2$NH$_2$); 3.93 (dd, J=7, 9 Hz, 1H, H-4 trans); 4.28 (dd, J=9, 9 Hz, 1H, H-4 cis); 5.00 (m, 1H, H-5); 8.05 (s, 2H, pyridyl H-3,4); 8.5 (m, 3H, NH$_2$, pyridyl H-6).

EXAMPLE XV (5S)3-(5-Bromo-pyridin-2-yl)-5-((tert-butoxy)carbonyl)aminomethyl-oxazolidin-2-one

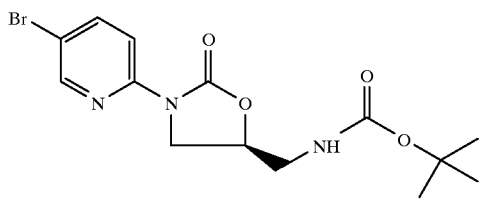

4.7 g (15 mmol) of the compound of Example XIV are suspended in 100 ml of CH$_2$Cl$_2$. 2.2 ml (16 mmol) of triethylamine are then added and a solution is formed. It is cooled to 0° C. 3.5 g (16 mmol) of Boc anhydride are then added in such a way that the temperature does not exceed +5° C., and the mixture is subsequently stirred overnight at room temperature. The organic phase is washed with saturated NaCl solution, dried over MgSO$_4$ and concentrated to give 5.4 g (97% of theory) of product in the form of a white solid.

M.p.: 184° C.

R$_f$ value (petroleum ether:ethyl acetate 10:4)=0.30

EXAMPLE XVI (5S)-3-(5-[3-Pyridyl]-pyridin-2-yl)-5-((tert-butoxy)carbonyl)aminomethyl-oxazolidin-2-one

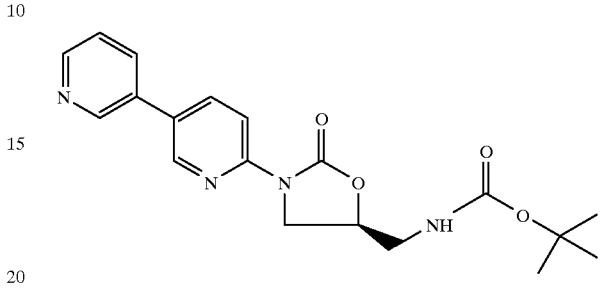

5.2 g (14.24 mmol) of the compound of Example XV and 2.81 g of diethyl-(3-pyridyl)-borane are placed in 100 ml of absolute THF under argon. A solution of 0.5 g (0.43 mmol) of [(PPh$_3$)$_4$Pd] in 90 ml of THF and 4.9 ml (9.83 mmol) of 2M sodium carbonate solution are added. The mixture is stirred for 5 days under reflux. After cooling, 10 g of kieselguhr are added and the mixture is concentrated. The residue is transferred to a column packed with silica gel and eluted with ethyl acetate.

4 g (76% of theory) of the title compound are obtained.

M.p.: 163° C.

R$_f$ value=0.36 (CH$_2$Cl$_2$:MeOH 100:5)

EXAMPLE XVII (5S)-3-(5-[3-Pyridyl]-pyridin-2-yl)-5-aminomethyl-oxazolidin-2-one trihydrochloride

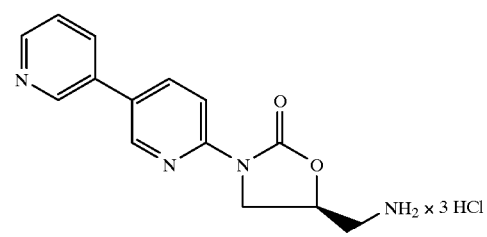

3.8 g (10.3 mmol) of the compound of Example XVI are suspended in 25 ml of dioxane. 32.1 ml of a 4M solution of HCl in dioxane are added and the mixture is stirred overnight at room temperature. It is concentrated and the residue is extracted by stirring with ether. The solid is then filtered off with suction on a frit and rinsed with ether. It is dried under high vacuum to give 3.7 g (95% of theory) of the title compound.

M.p.: >250° C.

MS (EI): 271 (M$^+$), 172

$^1$H NMR (200 MHz, DMSO-d$_6$): δ=9.35 (bs, 1H); 8.93 (m, 3H); 8.6 (broad, 3H); 8.42 (dd, J=9, J=3, 1H); 8.24 (d, J=9, 1H); 8.11 (dd, J=7.5, J=6.5, 1H); 6.7–5.3 (broad, 2H); 5.06 (m, 1H); 4.38 (tr, J=10, 1H); 4.03 (dd, J=10, J=7.5, 1H); 3.29 (m, 2H).

The compounds listed in Table II were prepared analogously to the instructions of Examples XII to XVII:

TABLE II

[Structure: A—N(oxazolidinone ring)—CH2—NH2 × HCl]

| Ex. no. | A | M.p. (° C.) | R_f/Solvent (ratio) | Yield (% of theory) |
|---|---|---|---|---|
| XVIII | 2-pyridyl-5-methylthiophene | — | — | 95 |
| XIX | 4-pyridyl-5-methylthiophene | — | — | 94 |
| XX | 3-pyridyl-5-methylthiophene | — | — | 94 |
| XXI | 2,6-dimethylpyridyl | — | 0.21, III (9:1) | 75 |
| XXII | 3-methylthiophene | 272 with decomp. | 0.13, III (9:1) | 61 |
| XXIII | 6-methylquinolinyl | 80 | 0.12, II (4:1) | 87 |

The compounds listed in Table III are prepared analogously to the instructions of Examples I to VI:

TABLE III

[Structure: A—N(C=O)—O—CH2—CH(OH)—]

| Ex. no. | A | M.p. (° C.) | R_f I (ratio) | Yield (% of theory) |
|---|---|---|---|---|
| XXIV | 2-propoxy-5-(5-methylthien-2-yl)pyridyl | 172 | 0.63 (100:1) | 94 |

TABLE III-continued

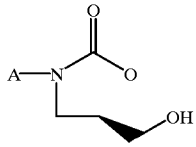

| Ex. no. | A | M.p. (° C.) | $R_f$ I (ratio) | Yield (% of theory) |
|---|---|---|---|---|
| XXV | (butoxy-pyridinyl-methylthiophene) | 177 | 0.62 (100:1) | 92 |
| XXVI | (methyl-pyridinyl-methylthiophene) | 217 | — | 83 |
| XXVII | (isopropoxy-pyridinyl-methylthiophene) | 206 | — | 99 |
| XXVIII | (pyrazinyl-methylthiophene) | 210 with decomp. | — | 76 |
| XXIX | (ethyl-pyridinyl-methylthiophene) | 112 with decomp. | — | 94 |
| XXX | (methoxy-pyridazinyl-methylthiophene) | 201 with decomp. | — | 80 |
| XXXI | (methoxy-pyridinyl-methylthiophene) | — | — | 99 |
| XXXII | (bipyridinyl-methyl) | 186 with decomp. | 0.16 (100:5) | 67 |

The compounds listed in Table IV are prepared analogously to the instructions of Example XIV and are isolated in the form of the free bases after aqueous working-up:

TABLE IV

| Ex. no. | A | M.p. (° C.) | R_f Solvent (ratio) | Yield (% of theory) |
|---|---|---|---|---|
| XXXIII | propoxy-pyridine-thiophene-methyl | — | — | 70 |
| XXXIV | butoxy-pyridine-thiophene-methyl | — | — | 46 |
| XXXV | 6-methyl-pyridine-thiophene-methyl | 168 with decomp. | 0.1, I (100:5) | 83 |
| XXXVI | isopropoxy-pyridine-thiophene-methyl | — | — | 91 |
| XXXVII | pentyl-pyridine-thiophene-methyl | — | 0.15, I (100:1) | 64 |
| XXXVIII | pyrazine-thiophene-methyl | — | 0.42, I* (10:1) | 47 |
| XXXIX | ethyl-pyridine-thiophene-methyl | 132 | 0.25, I* (10:1) | 64 |
| XL | methoxy-pyridazine-thiophene-methyl | — | — | 32 |
| XLI | methoxy-pyridine-thiophene-methyl | — | — | 53 |
| XLII | pyridine-pyridine-methyl | — | 0.08, I (10:1) | 56 |

*+0.1% NH$_3$.H$_2$O

Preparatory Examples

EXAMPLE 1

(5R)-3-(5-(2-Pyridyl)thien-2-yl)-5-ethoxycarbonyl-aminomethyl-oxazolidin-2-one

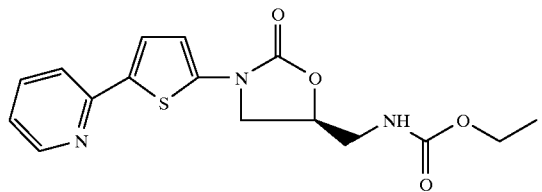

2 ml of methylene chloride and 0.33 ml (2.4 mmol) of triethylamine are added to 348 mg (1 mmol) of the compound of Example XXVIII. The resulting reaction mixture is cooled to 0° C. and 115 μl (1.2 mmol) of ethyl chloroformate are added. The mixture is allowed to warm up to room temperature overnight, concentrated and chromatographed on silica gel (methylene chloride:methanol 100:2).

Yield: 170 mg (49% of theory)

M.p.: 187° C. with decomp.

$R_f$=0.48 (I, 100:5)

MS (EI): 348 (M+H)$^+$(100%)

The compounds listed in Table 1 are prepared analogously to the instructions of Example 1:

TABLE 1

| Ex. no. | A | R$^1$ | M.p. (° C.) | R$_f$ Solvent (ratio) | Yield (%) |
|---|---|---|---|---|---|
| 2 | 2-pyridyl-thien-2-yl | —CO—CH$_2$Cl | 250 with decomp. | 0.34, I (100:5) | 8 |
| 3 | 2-pyridyl-thien-2-yl | —CO—OCH$_3$ | 174 with decomp. | 0.11, I (100:5) | 15 |
| 4 | 2-pyridyl-thien-2-yl | —SO$_2$—CH$_3$ | 177 with decomp. | | 45 |
| 5 | 2-pyridyl-thien-2-yl | —CO—NH$_2$ | 170 with decomp. | 0.1, I (100:5) | 60 |
| 6 | 2-pyridyl-thien-2-yl | —CO—CF$_3$ | 211 with decomp. | 0.45, I (100:5) | 60 |
| 7 | 2-pyridyl-thien-2-yl | —CO—CH$_2$F | 155 with decomp. | 0.27, I (100:5) | 84 |

TABLE 1-continued
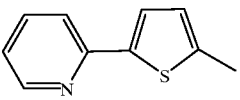
| Ex. no. | A | R¹ | M.p. (° C.) | $R_f$ Solvent (ratio) | Yield (%) |
|---|---|---|---|---|---|
| 8 | 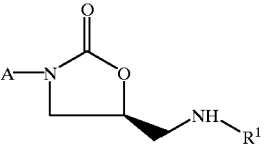 | 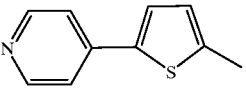 | 141 | 0.45, I (10:1) | 90 |
| 9 | 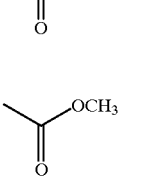 | 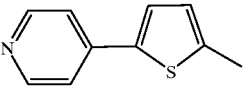 | 183 with decomp. | 0.14, I (100:5) | 84 |
| 10 | 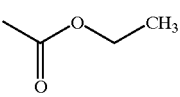 | 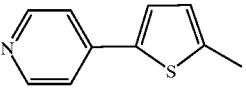 | 187 with decomp. | | 27 |
| 11 | 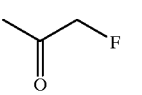 | 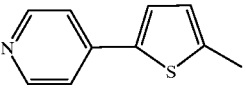 | 203 with decomp. | | 19 |
| 12 | 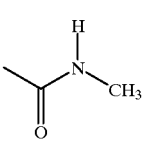 | 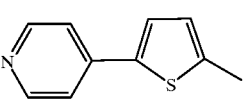 | 192 with decomp. | 0.45, I (10:1) | 38 |
| 13 | 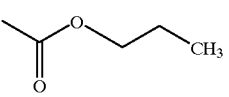 | 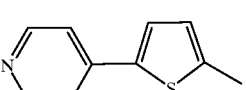 | 165 with decomp. | | 27 |
| 14 | 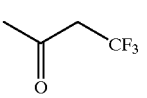 | 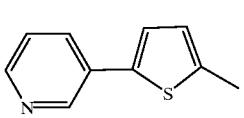 | 187 with decomp. | | 6 |
| 15 | 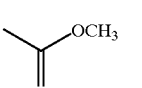 | 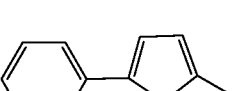 | 159 | 0.24, I (100:5) | 38 |
| 16 | 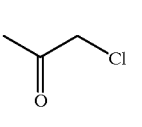 | 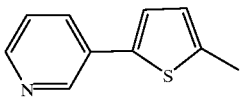 | 253 with decomp. | 0.34, I (100:5) | 8 |
| 17 | 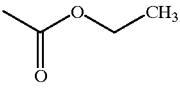 | | 164 with decomp. | 0.31, I (100:5) | 34 |

TABLE 1-continued

| Ex. no. | A | R[1] | M.p. (° C.) | R$_f$ Solvent (ratio) | Yield (%) |
|---|---|---|---|---|---|
| 18 | 3-pyridyl-(5-methylthien-2-yl) | -C(O)-CH$_2$F | 175 with decomp. | 0.3, I (100:5) | 21 |
| 19 | 3-pyridyl-(5-methylthien-2-yl) | -C(O)-NHCH$_3$ | 205 with decomp. | 0.4, I (10:1) | 25 |
| 20 | 3-pyridyl-(5-methylthien-2-yl) | -C(O)-O-CH$_2$CH$_3$ | 194 with decomp. | 0.58, I (10:1) | 35 |
| 21 | 3-pyridyl-(5-methylthien-2-yl) | -C(O)-CF$_3$ | 194 with decomp. |  | 11 |
| 22 | 2,6-dimethylpyridin-3-yl | -C(O)-NHCH$_3$ | 161 | 0.42, I (9:1) | 33 |
| 23 | 3-methylthien-2-yl | -C(O)-NHCH$_3$ | 145 | 0.41, I (9:1) | 74 |
| 24 | quinolin-6-yl | -C(O)-NHCH$_3$ | 107 | 0.26, I (9:1) | 48 |
| 25 | 3-bromo-2-methyl-6-methylpyridin-... | -C(O)-OCH$_3$ | 121 | 0.40, I (95:5) | 49 |
| 26 | 3-(pyridin-3-yl)-2-methyl-6-methylpyridin-yl × 2 HCl | -C(O)-OCH$_3$ | 125 | 0.24, I (95:5) | 56 |

TABLE 1-continued

| Ex. no. | A | R¹ | M.p. (° C.) | $R_f$ Solvent (ratio) | Yield (%) |
|---|---|---|---|---|---|
| 27 | butoxy-pyridine-thiophene-methyl | -C(=O)-O-CH₃ | 184 | 0.5, I (100:5) | 71 |
| 28 | propoxy-pyridine-thiophene-methyl | -C(=O)-O-CH₃ | 184 | 0.48, I (100:5) | 75 |
| 29 | H₃C-pyridine-thiophene-methyl | -C(=O)-O-CH₃ | 187 | 0.63, I (10:1) | 49 |
| 30 | propoxy-pyridine-thiophene-methyl | -C(=O)-NH₂ | 242 with decomp. | 0.52, I (10:1) | 72 |
| 31 | butoxy-pyridine-thiophene-methyl | -C(=O)-NH₂ | 242 with decomp. | 0.45, I (10:1) | 77 |
| 32 | H₃C-pyridine-thiophene-methyl | -C(=O)-NH₂ | 254 with decomp. | 0.27, I (10:1) | 49 |
| 33 | propoxy-pyridine-thiophene-methyl | -C(=O)-NH-CH₃ | 224 with decomp. | 0.59, I (10:1) | 86 |
| 34 | butoxy-pyridine-thiophene-methyl | -C(=O)-NH-CH₃ | 223 with decomp. | 0.63, I (10:1) | 87 |
| 35 | ethoxy-pyridine-thiophene-methyl | -C(=O)-O-CH₃ | 177 with decomp. | — | 28 |
| 36 | ethoxy-pyridine-thiophene-methyl | -C(=O)-NH₂ | — | — | 47 |
| 37 | H₃C-pyridine-thiophene-methyl | -C(=O)-O-CH₂CH₃ | 178 | — | 75 |

TABLE 1-continued

| Ex. no. | A | R¹ | M.p. (° C.) | R_f Solvent (ratio) | Yield (%) |
|---|---|---|---|---|---|
| 38 | 5-(6-methylpyridin-3-yl)-2-methylthiophene | -C(=O)-N(H)CH₃ | 218 with decomp. | 0.5, I (10:1) | 74 |
| 39 | 5-(6-methylpyridin-3-yl)-2-methylthiophene | -C(=O)-CH₂F | 188 with decomp. | 0.48, I (10:1) | 36 |
| 40 | 5-(6-methylpyridin-3-yl)-2-methylthiophene | -C(=O)-CF₃ | >210 with decomp. | 0.49, I (10:1) | 28 |
| 41 | 5-(6-isopropoxypyridin-3-yl)-2-methylthiophene | -C(=O)-OCH₃ | 140 | 0.6, I (20:1) | 49 |
| 42 | 5-(6-isopropoxypyridin-3-yl)-2-methylthiophene | -C(=O)-NH₂ | 204 with decomp. | 0.2, I (20:1) | 65 |
| 43 | 5-(6-pentylpyridin-3-yl)-2-methylthiophene | -C(=O)-OCH₃ | 175 | 0.57, I (10:1) | 29 |
| 44 | 2-(5-methylthien-2-yl)pyrazine | -C(=O)-OCH₃ | 134 with decomp. | 0.34, I (100:5) | 60 |
| 45 | 2-(5-methylthien-2-yl)pyrazine | -C(=O)-NH₂ | 233 with decomp. | — | 84 |
| 46 | 2HCl· 2-(5-methylthien-2-yl)pyrazine | -C(=O)-OCH₃ | 258 with decomp. | — | 99 |
| 47 | 5-(6-ethylpyridin-3-yl)-2-methylthiophene | -C(=O)-OCH₃ | 182 | 0.39, I (10:1) | 54 |

TABLE 1-continued

| Ex. no. | A | R¹ | M.p. (° C.) | R_f Solvent (ratio) | Yield (%) |
|---|---|---|---|---|---|
| 48 | 6-ethyl-pyridin-3-yl-(5-methylthiophen-2-yl) | -C(O)-NH₂ | 135 with decomp. | 0.67, I (100:5) | 16 |
| 49 | 6-methoxy-pyridazin-3-yl-(5-methylthiophen-2-yl) | -C(O)-O-CH₃ | 155 | 0.25, I (20:1) | 12 |
| 50 | 6-methoxy-pyridin-3-yl-(5-methylthiophen-2-yl) | -C(O)-O-CH₃ | 173 | 0.45, I (20:1) | 11 |
| 51 | 6-methoxy-pyridin-3-yl-(5-methylthiophen-2-yl) | -C(O)-NH₂ | 205 with decomp. | 0.1, I (100:1) | 30 |
| 52 | 6'-methyl-[3,2'-bipyridin]-5-yl | -C(O)-O-CH₃ | 211 with decomp. | — | 30 |
| 53 | 6'-methyl-[4,2'-bipyridin]-5-yl | -C(O)-O-CH₃ | 187 with decomp. | 0.28, I, (10:1) | 31 |
| 54 | 6-methyl-[3,3'-bipyridin]-5-yl | —CO—NH₂ | 189 | 0.38, I, (10:1) | 24 |
| 55 | pyridin-3-yl-(5-methylthiophen-2-yl) | —CO—NH₂ | 218 | 0.42, I, (10:1) | 33 |
| 56 | pyridin-3-yl-(5-methylthiophen-2-yl) | —CO—NH₂ | 152 | 0.36, I, (10:1) | 7 |
| 57 | 6'-methyl-[3,3'-bipyridin]-5-yl | —CO₂—C(CH₃)₃ | 163 | 0.36, I (100:5) | 76 |

TABLE 1-continued

[Structure: oxazolidinone with A-N substituent and CH₂-NH-R¹ side chain]

| Ex. no. | A | R¹ | M.p. (° C.) | R_f Solvent (ratio) | Yield (%) |
|---|---|---|---|---|---|
| 58 | 5-Br-pyridin-2-yl (Br—[pyridine]—) | —C(=O)—O—CH₃ (methyl carbamate) | — | 0.38, II (1:1) | 36 |
| 59 | 2-Br-pyridin-5-yl | —C(=O)—O—CH₃ | 131 | — | 31 |

The compounds listed in Table 2 were prepared analogously to the instructions of Example XVI:

TABLE 2

| Ex. no. | A | R¹ | F (° C.) | R_f | Yield (% of theory) |
|---|---|---|---|---|---|
| 60 | 3,3'-bipyridine (6-methyl) | —C(=O)—O—CH₃ | — | 0.11, I (10:1) | 68 |
| 61* | 4,3'-bipyridine (6'-methyl) | —C(=O)—O—CH₃ | — | 0.33, I (10:1) | 35 |
| 62* | 6-methyl-pyridin-3-yl—pyridin-3'-yl (H₃C—) | —C(=O)—O—CH₃ | — | 0.33, I (10:1) | 56 |
| 63* | CH₃-pyridyl—pyridyl | —C(=O)—O—CH₃ | 165 | 0.28, I (10:1) | 49 |
| 64* | CH₃-pyrimidinyl—pyridyl | —C(=O)—O—CH₃ | 198 | 0.38, I (10:1) | 50 |

*Compounds 61 to 64 were prepared analogously to the instructions of XVI from the appropriate trimethylstannyl compounds.

EXAMPLE 65

(5S)-3-(5-(4-Pyridyl)-pyridin-2-yl)-3-(methoxycarbonylaminomethyl)-2-oxazolidinone hydrochloride

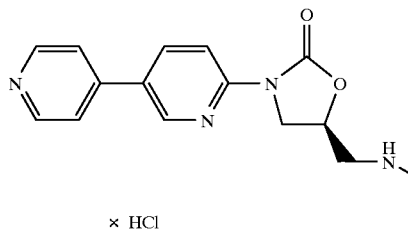

× HCl 2.04 ml (8.16 mmol) of 4N HCl in dioxane and then 200 ml of ether are added to a solution of 500 mg (1.6 mmol) of the compound of Example 61 in 60 ml of dioxane. The precipitate formed is filtered off with suction, washed with ether and dried under high vacuum.

Yield: 0.555 g (90%)

$^1$H NMR (200 MHz, DMSO-$d_6$): δ=8.9–9.2 (m, 3H); 8.45–8.55 (m, 3H); 8.30 (bt, 1H, NH); 8.20 (d, 2H); 4.70 (m, 1H); 4.30 (dd, 1H); 3.95 (dd, 1H); 3.52 (s, 3H); 3.45 (m, 2H).

The compounds listed in Table 3 were prepared analogously to the instructions of Example 65:

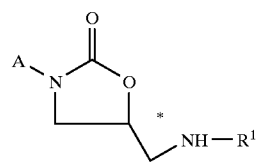

(I)

in which

R$^1$ represents a radical of the formula D—R$^2$, —CO—R$^3$ or —CO—NR$^4$R$^5$;

in which

D represents —CO$_2$— or —SO$_2$—;

R$^2$ represents phenyl or linear or branched alkyl having up to 7 carbon atoms;

R$^3$ represents trifluoromethyl or linear or branched alkyl having up to 6 carbon atoms, which alkyl is substituted by halogen or trifluoromethyl; and R$^4$ and R$^5$ are identical or different and represent hydrogen, phenyl, or linear or branched alkyl having up to 5 carbon atoms;

A represents a pyridyl radical, which is optionally substituted by up to 3 identical or different substituents selected from the group consisting of carboxyl, halogen, cyano, mercapto, formyl, trifluoromethyl, nitro, linear or branched alkoxy, alkoxycarbonyl, alkylthio or acyl, each of which has up to 6 carbon atoms, and linear or branched alkyl, which is, in turn, option-

TABLE 3

| Ex. no. | A | R$^1$ | M.p. (° C.) | Yield (% of theory) |
|---|---|---|---|---|
| 66 | CH$_3$-pyridyl-pyridyl- | -C(O)OCH$_3$ | 239° C., with decomp. | 93% |
| 67 | pyridyl-pyridyl- | -C(O)OCH$_3$ | 227° C., with decomp. | 87% |
| 68 | CH$_3$-pyrimidyl-pyridyl- | -C(O)OCH$_3$ | 207° C., with decomp. | 70% |

We claim:

1. A heteroaryl-oxazolidinone compound of the formula (I):

ally substituted by hydroxyl, linear or branched alkoxy or acyl, each of which alkoxy or acyl has up to 5 carbon atoms, or by a group of the formula —NR$^6$R$^7$;

in which

R⁶ and R⁷ are identical or different and represent hydrogen, cycloalkyl having 3 to 6 carbon atoms, linear or branched alkyl having up to 5 carbon atoms, or phenyl; or R⁶ and R⁷, together with the nitrogen atom to which they are attached, form a 5- or 6-membered saturated heterocycle optionally comprising another heteroatom selected from the group consisting of N, S and O, which heterocycle, in turn, is optionally substituted, optionally on another nitrogen atom thereof if present, by linear or branched alkyl or acyl, each of which has up to 3 carbon atoms; and/or the pyridyl radical is optionally substituted by a group of the formula —NR⁶'R⁷';

wherein

R⁶' and R⁷' are identical or different and independently have the meaning given above for R⁶ and R⁷; and/or the pyridyl radical is optionally substituted by alkenylphenyl, which has 2 to 8 carbon atoms in the alkenyl portion, phenyl or a 5- or 6-membered saturated or unsaturated heterocycle having up to 3 heteroatoms independently selected from the group consisting of S, N and O, which alkenylphenyl, phenyl or heterocycle, in turn, is optionally substituted by a group of the formula —CONR⁸R⁹, —NR¹⁰R¹¹, —NR¹²—S(O)₂—R¹³, R¹⁴R¹⁵N—SO₂— or R¹⁶—S(O)$_a$—;

in which a represents the number 0, 1 or 2;

R⁸, R⁹, R¹², R¹⁴ and R¹⁵ are identical or different and represent hydrogen, linear or branched alkyl having up to 6 carbon atoms or phenyl;

R¹⁰ and R¹¹ are identical or different and independently have the meaning given above for R⁶ and R⁷; and R¹³ and R¹⁶ are identical or different and are linear or branched alkyl having up to 4 carbon atoms or phenyl, which phenyl is optionally substituted by linear or branched alkyl having up to 4 carbon atoms; and/or the alkenylphenyl, phenyl or heterocycle is optionally substituted by up to 2 identical or different substituents selected from the group consisting of carboxyl, halogen, cyano, mercapto, formyl, trifluoromethyl, nitro, phenyl, linear or branched alkoxy, alkoxycarbonyl, alkylthio or acyl, each of which has up to 6 carbon atoms, and linear or branched alkyl having up to 6 carbon atoms, which alkyl is, in turn, optionally substituted by hydroxyl, linear or branched alkoxy or acyl, each of which has up to 5 carbon atoms, or by a group of the formula —NR¹⁷R¹⁸;

in which

R¹⁷ and R¹⁸ are identical or different and independently have the meaning given above for R⁶ and R⁷; and/or the pyridyl radical is optionally substituted by a radical of the formula:

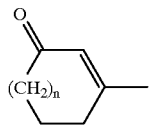

wherein n represents the number 0, 1 or 2;

or a stereoisomer, stereoisomer mixture or salt thereof.

2. The compound according to claim 1, in which

R¹ represents a radical of the formula D—R², —CO—R³ or —CO—NR⁴R⁵;

in which

D represents —CO₂— or —SO₂—;

R² represents phenyl or linear or branched alkyl having up to 5 carbon atoms;

R³ represents trifluoromethyl or linear or branched alkyl having up to 5 carbon atoms, which alkyl is substituted by fluorine, chlorine, bromine or trifluoromethyl; and R⁴ and R⁵ are identical or different and represent hydrogen, phenyl, or linear or branched alkyl having up to 4 carbon atoms; and A represents a pyridyl radical, which is optionally substituted by up to 3 identical or different substituents selected from the group consisting of fluorine, chlorine, bromine, linear or branched alkyl, acyl or alkoxy, each of which has up to 5 carbon atoms, phenyl, pyrimidyl, pyridazinyl or pyridyl, which phenyl, pyrimidyl, pyridazinyl or pyridyl is, in turn, optionally substituted by linear or branched alkyl, alkoxy or acyl, each of which has up to 5 carbon atoms, and a group of the formula —NR⁶R⁷;

in which

R⁶ and R⁷ are identical or different and represent hydrogen, phenyl, cyclopropyl, cyclobutyl, cyclopentyl, cyclohexyl or linear or branched alkyl having up to 4 carbon atoms;

or a stereoisomer, stereoisomer mixture or salt thereof.

3. The compound according to claim 1, in which

R¹ represents a radical of the formula D—R², —CO—R³ or —CO—NR⁴R⁵;

in which

D represents —CO₂— or —SO₂—;

R² represents phenyl or linear or branched alkyl having up to 4 carbon atoms;

R³ represents trifluoromethyl or linear or branched alkyl having up to 3 carbon atoms, which alkyl is substituted by fluorine, chlorine, bromine or trifluoromethyl; and R⁴ and R⁵ are identical or different and represent hydrogen, phenyl, or linear or branched alkyl having up to 3 carbon atoms; and A represents a pyridyl radical, which is optionally substituted by up to 2 identical or different substituents selected from the group consisting of chlorine, bromine, linear or branched alkyl or alkoxy, each of which has up to 5 carbon atoms, phenyl, pyrimidyl, pyridazinyl or pyridyl, which phenyl, pyrimidyl, pyridazinyl or pyridyl is, in turn, optionally substituted by linear or branched alkyl, alkoxy or acyl, each of which has up to 5 carbon atoms, and a group of the formula —NR⁶R⁷;

in which

R⁶ and R⁷ are identical or different and represent hydrogen, phenyl, cyclopropyl, cyclobutyl, cyclopentyl, cyclohexyl or linear or branched alkyl having up to 3 carbon atoms;

or a stereoisomer, stereoisomer mixture or salt thereof.

4. A compound according to claim 1 of the formula or a salt thereof.

5. A compound according to claim 1 of the formula or a salt thereof.

6. A compound according to claim 1 of the formula or a salt thereof.

7. A compound according to claim 1 of the formula or a salt thereof.

8. A compound according to claim 1 of the formula or a salt thereof.

9. A process for preparing a compound according to claim 1, said process comprising reacting a compound of the formula (II):

(II)

in which

A represents a pyridyl radical, which is optionally substituted by up to 3 identical or different substituents selected from the group consisting of carboxyl, halogen, cyano, mercapto, formyl, trifluoromethyl, nitro, linear or branched alkoxy, alkoxycarbonyl, alkylthio or acyl, each of which has up to 6 carbon atoms, and linear or branched alkyl, which is, in turn, optionally substituted by hydroxyl or linear or branched alkoxy or acyl, each of which alkoxy or acyl has up to 5 carbon atoms, or by a group of the formula —$NR^6R^7$;

in which $R^6$ and $R^7$ are identical or different and represent hydrogen, cycloalkyl having 3 to 6 carbon atoms, linear or branched alkyl having up to 5 carbon atoms, or phenyl; or $R^6$ and $R^7$, together with the nitrogen atom to which they are attached, form a 5- or 6-membered saturated heterocycle optionally comprising another heteroatom selected from the group consisting of N, S and O, which heterocycle, in turn, is optionally substituted, optionally on another nitrogen atom thereof if present, by linear or branched alkyl or acyl, each of which has up to 3 carbon atoms; and/or the pyridyl radical is optionally substituted by a group of the formula —$NR^{6'}R^{7'}$;

wherein $R^{6'}$ and $R^{7'}$ are identical or different and independently have the meaning given above for $R^6$ and $R^7$; and/or the pyridyl radical is optionally substituted by alkenylphenyl, which has 2 to 8 carbon atoms in the alkenyl portion, phenyl or a 5- or 6-membered saturated or unsaturated heterocycle having up to 3 heteroatoms independently selected from the group consisting of S, N and O, which alkenylphenyl, phenyl or heterocycle, in turn, is optionally substituted by a group of the formula —$CONR^8R^9$, —$NR^{10}R^{11}$, —$NR^{12}$—$S(O)_2$—$R^{13}$, $R^{14}R^{15}N$—$SO_2$— or $R^{16}$—$S(O)_a$—;

in which a represents the number 0, 1 or 2;

$R^8$, $R^9$, $R^{12}$, $R^{14}$ and $R^{15}$ are identical or different and represent hydrogen, linear or branched alkyl having up to 6 carbon atoms or phenyl;

$R^{10}$ and $R^{11}$ are identical or different and independently have the meaning given above for $R^6$ and $R^7$; and $R^{13}$ and $R^{16}$ are identical or different and are linear or branched alkyl having up to 4 carbon atoms or phenyl, which phenyl is optionally substituted by linear or branched alkyl having up to 4 carbon atoms; and/or the alkenylphenyl, phenyl or heterocycle is optionally substituted by up to 2 identical or different substituents selected from the group consisting of carboxyl, halogen, cyano, mercapto, formyl, trifluoromethyl, nitro, phenyl, linear or branched alkoxy, alkoxycarbonyl, alkylthio or acyl, each of which has up to 6 carbon atoms, and linear or branched alkyl having up to 6 carbon atoms, which alkyl is, in turn, optionally substituted by hydroxyl, linear or branched alkoxy or acyl, each of which has up to 5 carbon atoms, or by a group of the formula —NR$^{17}$R$^{18}$;

in which $R^{17}$ and $R^{18}$ are identical or different and independently have the meaning given above for $R^6$ and $R^7$; and/or the pyridyl radical is optionally substituted by a radical of the formula:

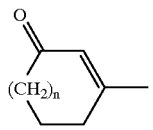

wherein n represents the number 0, 1 or 2;

with a compound of the formula (III):

$$R^1—E \qquad (III)$$

in which $R^1$ represents a radical of the formula D—R$^2$, —CO—R$^3$ or —CO—NR$^4$R$^5$;

in which

D represents —CO$_2$— or —SO$_2$—;

$R^2$ represents phenyl or linear or branched alkyl having up to 7 carbon atoms;

$R^3$ represents trifluoromethyl or linear or branched alkyl having up to 6 carbon atoms, which alkyl is substituted by halogen or trifluoromethyl; and $R^4$ and $R^5$ are identical or different and represent hydrogen, phenyl, or linear or branched alkyl having up to 5 carbon atoms; and E represents halogen, or linear or branched alkylthio, alkoxy or hydroxyalkoxycarbonyl, each of which has up to 5 carbon atoms;

in an inert solvent and optionally in the presence of a base; and optionally the compound is converted to its salt or, if already in salt form, freed from its salt; and optionally the compound or salt, if in the form of a racemic mixture, is resolved to an individual stereoisomer or a mixture of stereoisomers.

10. A pharmaceutical composition which comprises a compound according to claim 1 and a pharmaceutically suitable excipient.

11. A method of treating microbial infections to a host in need thereof which comprises administering an antimicrobility effective amount of a compound according to claim 1 to said host.

* * * * *

UNITED STATES PATENT AND TRADEMARK OFFICE
CERTIFICATE OF CORRECTION

PATENT NO. : 5,922,708
DATED : July 13, 1999
INVENTOR(S) : Bernd RIEDL, et al.

It is certified that error appears in the above-identified patent and that said Letters Patent is hereby corrected as shown below:

Column 45, lines 5-11, cancel the structure

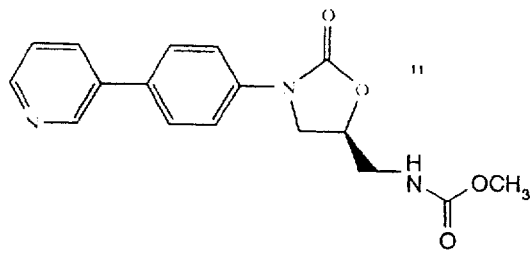

and substitute

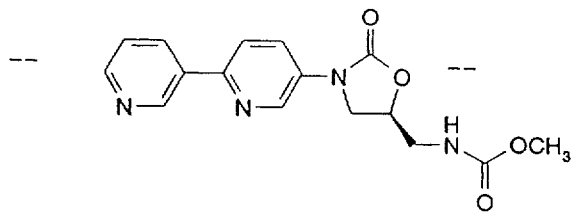

Signed and Sealed this

Fourth Day of January, 2000

Attest:

*Attesting Officer*

*Acting Commissioner of Patents and Trademarks*